United States Patent [19]

Kensey

[11] Patent Number: 4,790,813
[45] Date of Patent: * Dec. 13, 1988

[54] METHOD AND APPARATUS FOR SURGICALLY REMOVING REMOTE DEPOSITS

[75] Inventor: Kenneth R. Kensey, Hinsdale, Ill.

[73] Assignee: Intravascular Surgical Instruments, Inc., Frazer, Pa.

[*] Notice: The portion of the term of this patent subsequent to Dec. 23, 2003 has been disclaimed.

[21] Appl. No.: 868,969

[22] Filed: May 30, 1986

Related U.S. Application Data

[63] Continuation of Ser. No. 682,393, Dec. 17, 1984, Pat. No. 4,631,052, which is a continuation-in-part of Ser. No. 567,506, Jan. 3, 1984, Pat. No. 4,589,412.

[51] Int. Cl.$^4$ ............................................. A61B 17/32
[52] U.S. Cl. .................................... 604/22; 128/304; 128/305; 128/305.1
[58] Field of Search ..................... 128/304, 305, 305.1, 128/310, 755, 303 R; 604/22

[56] References Cited

U.S. PATENT DOCUMENTS

| | | | |
|---|---|---|---|
| 2,937,414 | 5/1960 | Kern ................................ | 128/310 X |
| 3,565,062 | 2/1971 | Kuris ................................ | 128/24 |
| 3,614,953 | 10/1971 | Moss ................................ | 604/27 X |
| 4,030,503 | 6/1977 | Clark ................................ | 128/304 |
| 4,203,444 | 5/1980 | Bonnell et al. .................... | 128/305 |
| 4,207,874 | 6/1980 | Choy ................................ | 128/6 |
| 4,273,128 | 6/1981 | Cary ................................ | 128/305 |
| 4,445,509 | 5/1984 | Auth ................................ | 128/305 |
| 4,445,892 | 5/1984 | Hussein et al. .................... | 604/101 |
| 4,522,206 | 6/1985 | Whipple et al. ................... | 128/305 X |

FOREIGN PATENT DOCUMENTS

| | | | |
|---|---|---|---|
| 2804015 | 8/1979 | Fed. Rep. of Germany ...... | 128/305 |
| 3231127 | 2/1984 | Fed. Rep. of Germany ...... | 128/305 |
| 605610 | 4/1978 | U.S.S.R. ............................ | 128/305 |
| 442795 | 9/1978 | U.S.S.R. ............................ | 128/305 |
| 938977 | 7/1982 | U.S.S.R. ............................ | 128/305 |

Primary Examiner—Michael H. Thaler
Attorney, Agent, or Firm—Caesar, Rivise, Bernstein, Cohen & Pokotilow, Ltd.

[57] ABSTRACT

Procedures and devices for opening restrictions, e.g., occulsions, in passageways, e.g., arteries, of living beings. The device basically comprises an elongated, flexible recanalization catheter arranged to be threaded through the passageway to the site of the restriction. The catheter includes a working head which is adapted to be moved, e.g., rotated, by turbine drive while the head is advanced into the restriction to effect its opening. Blocking apparatus is provided for use with the catheter to preclude any debris produced during the restriction opening procedure from flowing distally down the passageway. Profusion apparatus also provided to provide oxygenated fluid, drugs, contrast media or dyes into the passageway. One embodiment of the recanalization catheter is a combination device having different diameter sections for introduction into a large passageway within the body while the working head is located within a small remotely located passageway.

13 Claims, 5 Drawing Sheets

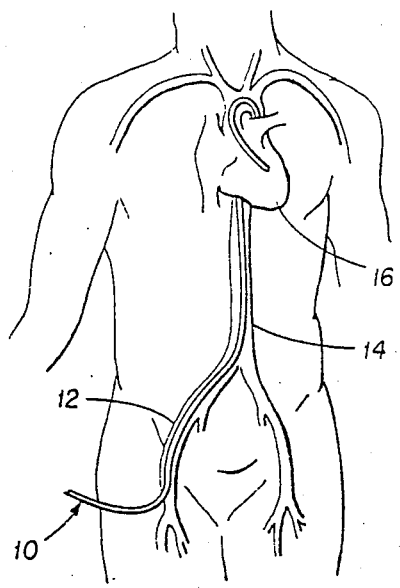
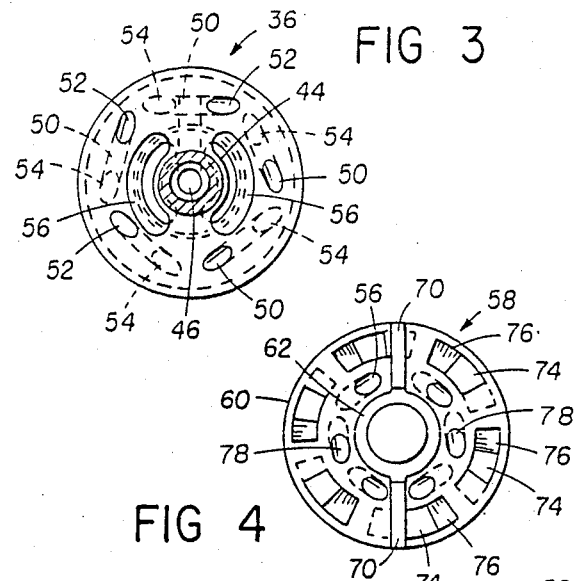
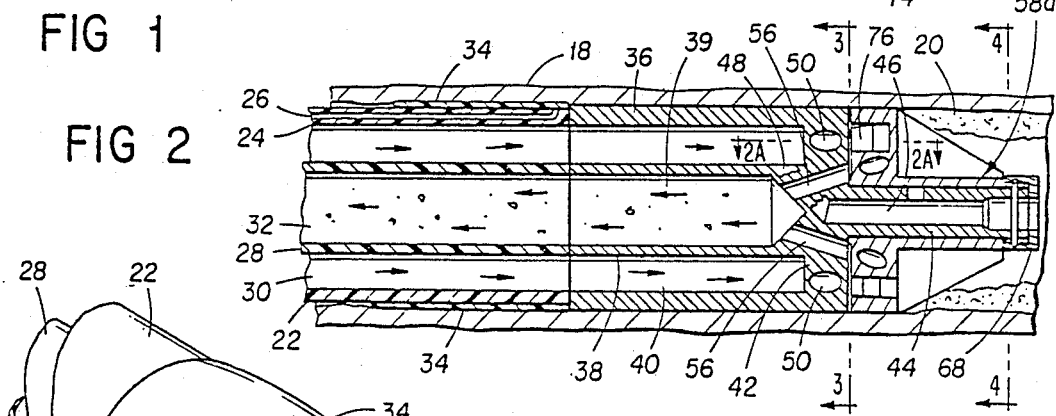
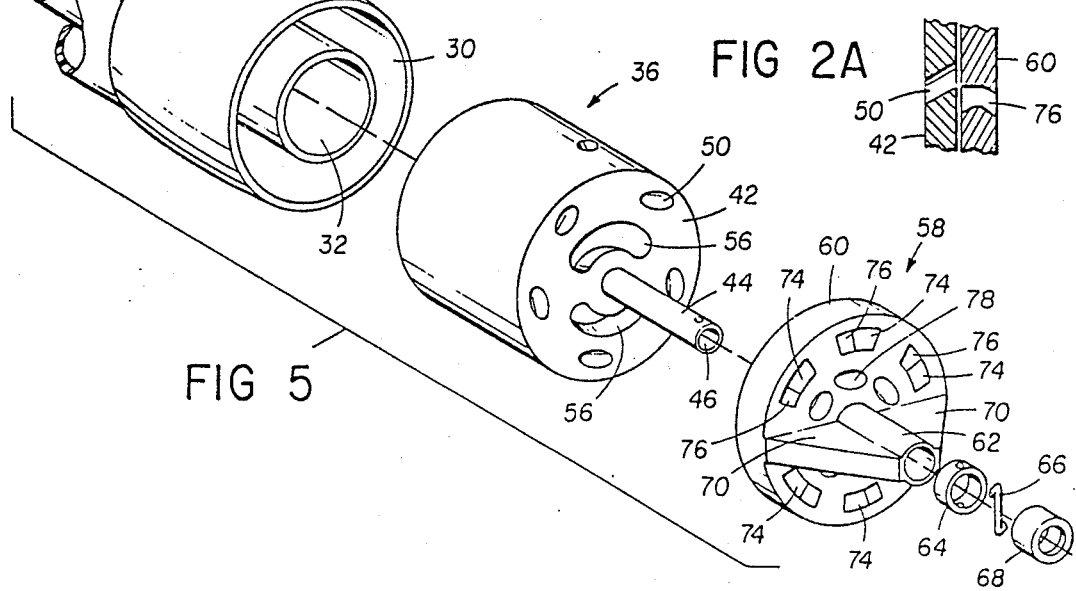

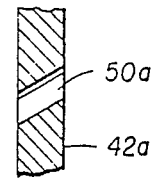
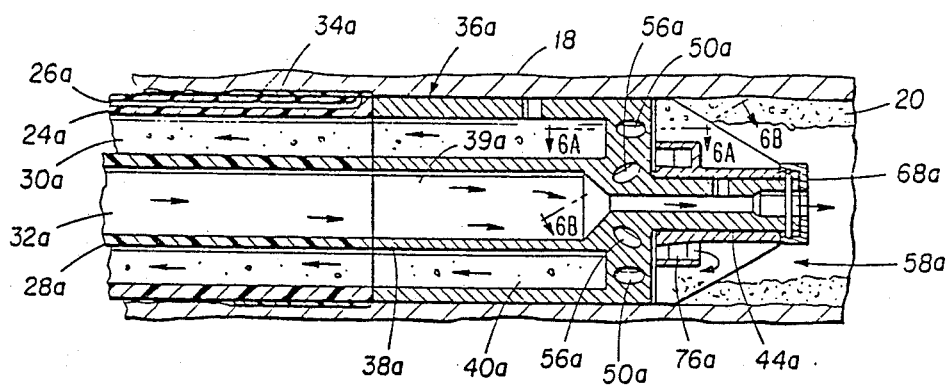
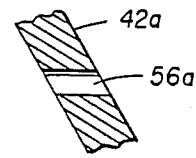
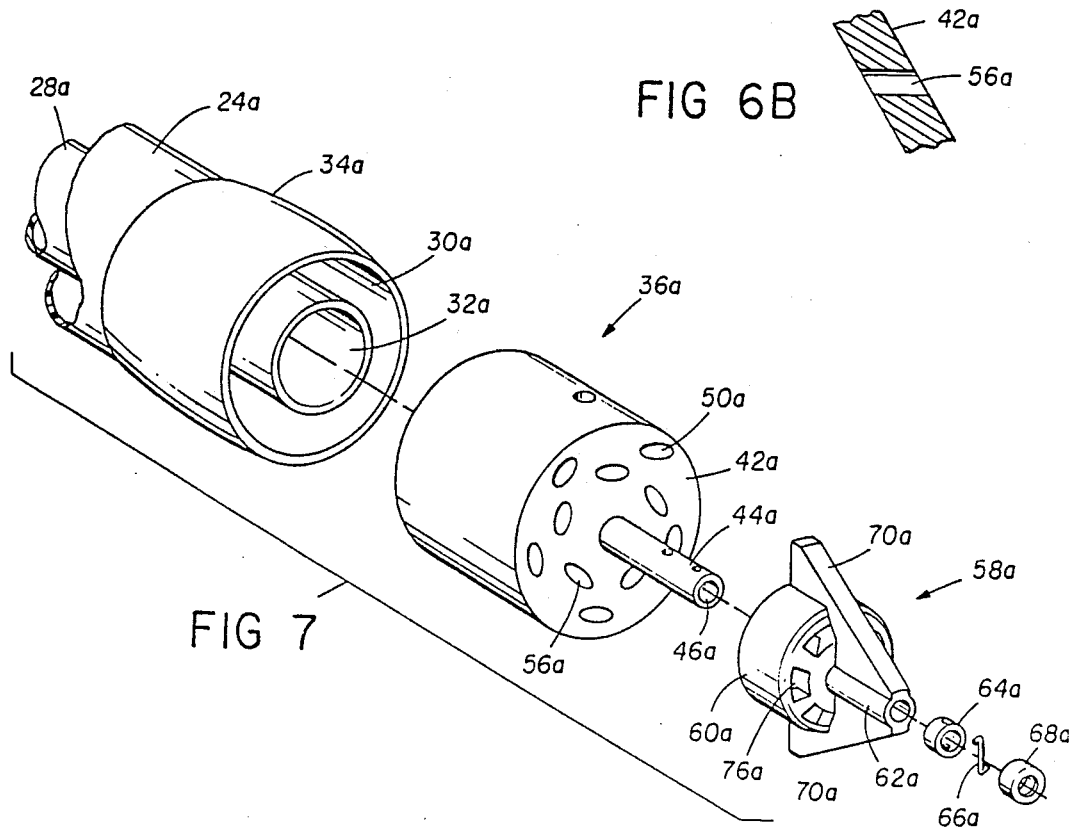

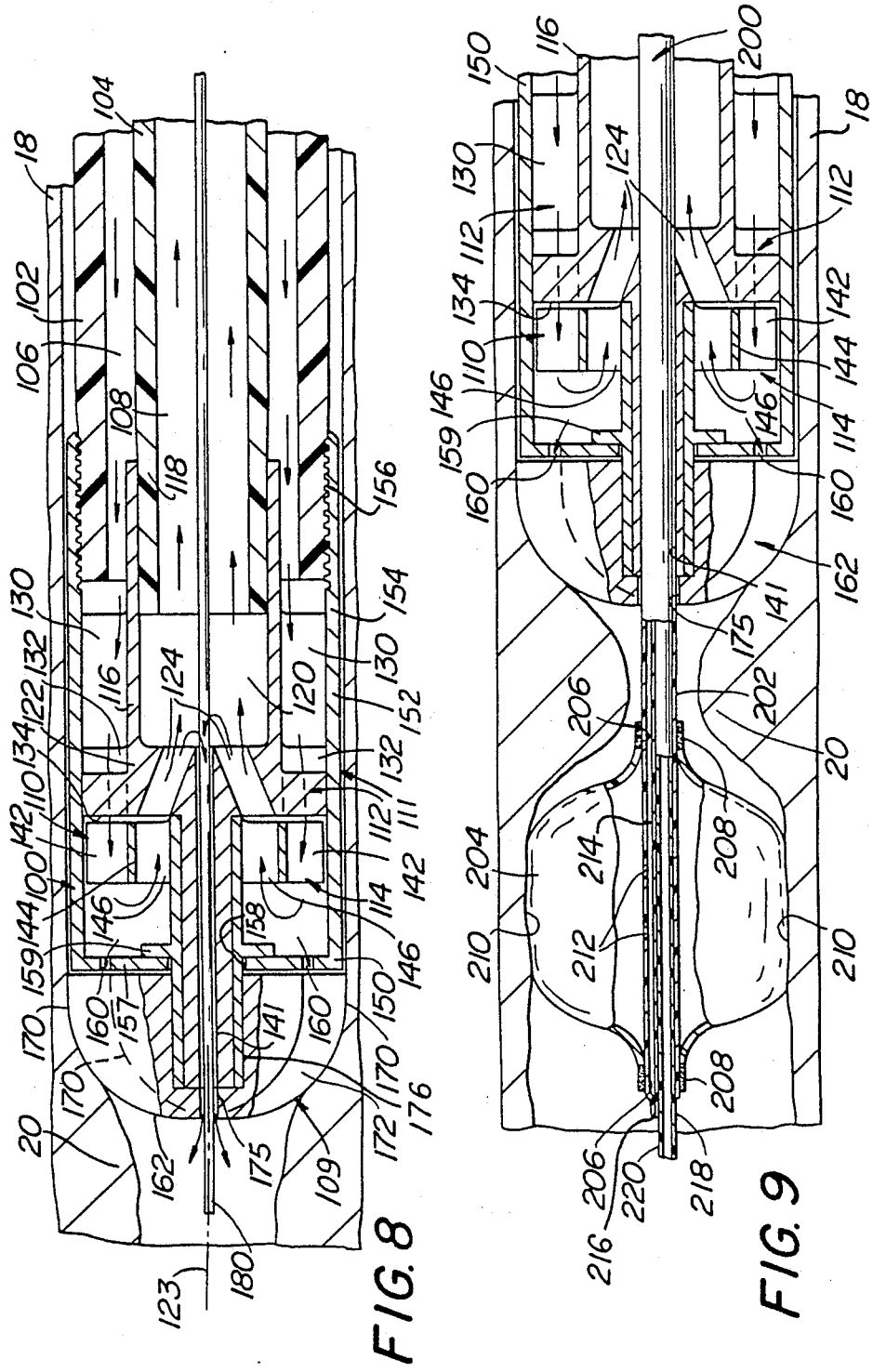

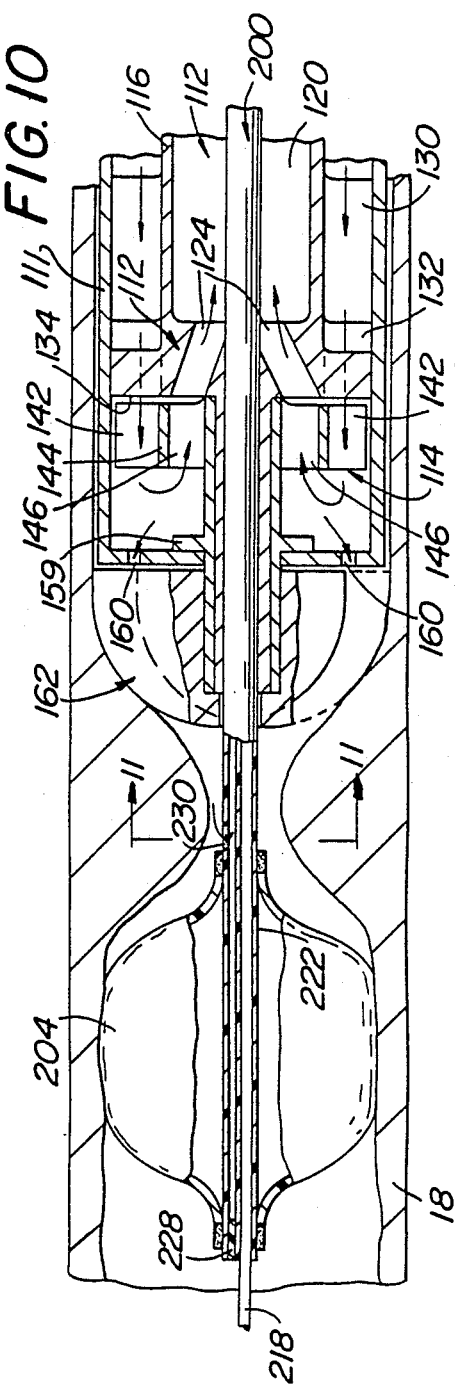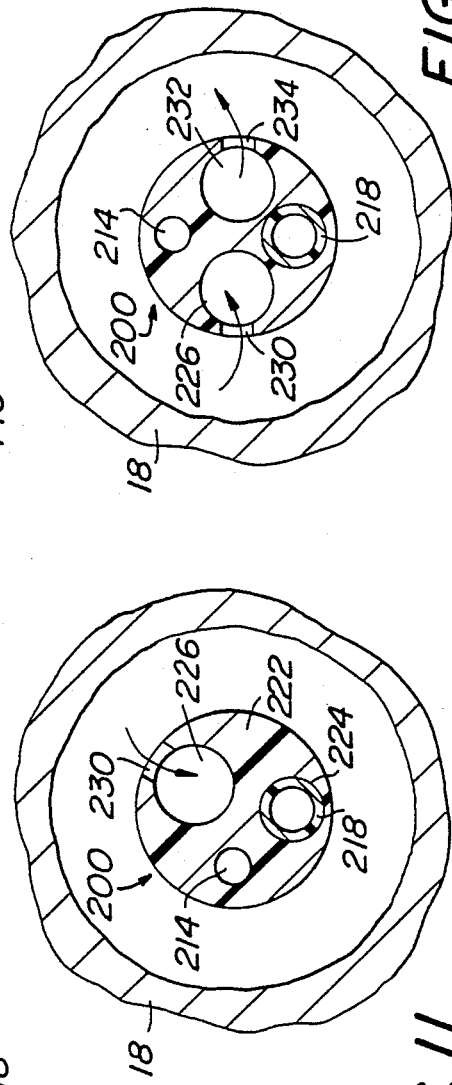

METHOD AND APPARATUS FOR SURGICALLY REMOVING REMOTE DEPOSITS

This application is a continuation of application Ser. No. 682,393 filed on Dec. 17, 1984, now U.S. Pat. No. 4,631,052 and entitled Method and Apparatus for Surgically Removing Remote Deposits, which in turn is a continuation-in-part of my U.S. patent application Ser. No. 567,506 filed on Jan. 3, 1984, entitled Method and Appoaratus for Surgically Removing Remote Deposits, now U.S. Pat. No. 4,589,412. The disclosures of both of said earlier applications are hereby incorporated by reference herein.

BACKGROUND OF THE INVENTION

One of the major causes of death in the United States is heart disease produced by atherosclerosis. In atherosclerosis, a plaque forms in the arteries which may involve only a segmental portion of the artery or can involve its entire circumference. This plaque is a "putty-like" or rock-hard material which, if allowed to accumulate, can completely occlude the artery. Also, the plaque can become dislodged from the artery wall and thereby serve as an embolus, or pieces of it may break off and emoblize. If complete blockage occurs, and the individual survives, sometimes small new vessels recanalize the area, but the ability of these small vessels to supply any appreciable volume of blood beyond the area of blockage is doubtful.

Coronary atherosclerotic narrowing or occlusion has been corrected in recent years most frequently by revascularization of the myocardium. This bypass surgery has become one of the most common surgical procedures performed in the United States. However, the exorbitant cost of myocardial bypass and the associated one to two week morbidity associated with such procedure has led to a procedure termed angioplasty in which an inflatable "balloon" at the end of a catheter is introduced at a selected point in the vascular system and passed into the coronary artery to the site of the occlusion and the plaque compressed by inflating the balloon. Angioplasty, however, is limited in scope of its use because of the variability and the texture of the atherosclerotic plaques and in the inherent limitations of the balloon itself. Moreover, angioplasty is not viewed as a permanent treatment and can result in complications such as artery blow-out, distal emboli spasm, etc.

Development of laser technology for treatment of atherosclerotic plaques is now being conducted, but such a technique, even if successfully developed, has significant limitations.

In a population where average age continues to increase, with a corresponding increase in atherosclerotic heart disease, there is an urgent need for an inexpensive, efficient, safe and effective means for the treatment of atherosclerosis. This urgent need is dictated by the fact that approximately one-fourth of those with atherosclerotic heart disease have as a first symptom sudden death, and each year in the United States alone a million people are diagnosed as having atherosclerotic heart disease. Moreover, a relatively small percentage of those affected with atherosclerotic heart disease are treatable surgically, and there is no indication that there will ever be developed any effective, preventative, pharmacologic treatment of atherosclerotic heart disease.

There is, therefore, a definite and almost urgent need for any technique or device that could produce percutaneous transluminal elimination of atherosclertoc plaques.

OBJECTS OF THE INVENTION

Accordingly it is a general object of the instant invention to overcome the disadvantages of the prior art by providing apparatus and methods for mechanically opening a restriction in a passageway, e.g., artery, of a living being.

It is a further object of this invention to provide apparatus and methods for efficiently opening a restriction in a passageway in a living being without significant damage to such passageway.

It is still a further object of this invention to provide apparatus and methods for mechanically opening a restriction in a passageway in a living being while preventing any material or debris produced during said procedure from blowing distally of said restriction.

It is still a further object of this invention to provide apparatus and methods for mechanically opening a restriction in a passageway in a living being while enabling fluids to prefuse distal tissues during said procedure.

It is still a further object of this invention to provide apparatus and methods for mechanically opening a restriction in a small pasageway of a living being utilizing a catheter introduced into a larger passageway remote from the site of the restriction.

SUMMARY OF THE INVENTION

These and other objects of this invention are acheived by providing a method and apparatus for opening a restriction, e.g., an occlusion, formed of a material (either hard, soft or a combinations thereof) inside of a passageway, e.g., an artery, of a living being. The apparatus and method of this invention effect a dynamic form of intravascular angioplasty in that the opening is created dynamically by use of a moving working head either cutting and removing the material forming the restriction or by mechnically beating or otherwise agitating or disturbing the material to form the opening.

In accordance with one aspect of the invention the application comprises a flexible recanalization catheter having a distal portion at which a movable working head is located. The working head is fluid-driven to cause it to move (e.g., rotate) with respect to the material making up the restriction. The catheter with the moving working head is advanced into the material to open the restriction.

In accordance with another aspect of the invention the working head comprises a cutting head, which is preferably rotary.

In accordance with still another aspect of the invention positive pressure is provided to the passageway adjacent to the restriction to expedite the safe opening of the restriction without damage to the passageway.

In accordance with yet another aspect of the invention a fluid such as the working head driving fluid or some other fluid which may be oxygenated and/or contain a drug, and/or a contrast medium or dye is introduced into the passageway adjacent the restriction.

In accordance with still a fruther aspect of the invention means are provided to constrain a substantial portion of the fluid which drives the working means within the catheter to preclude the egress thereof into the passageway.

In accorance with still a further aspect of the invention blocking means are provided for location distally of the restriction to preclude any material which may be removed during the restriction opening procedure from flowing through the passageway distally of the blocking means.

In accordance with yet a further aspect of this invention a flexible recanalization catheter having two different diameter sections is used so that the smaller diameter section, which includes the working head, can be disposed within a small diameter passageway containing a restriction whole the large diameter section is disposed within a larger diameter remotely located passageway. The first section includes a proximal end portion, a distal end portion with the working means located thereat, and first drive means. The second section includes second drive means and having a distal end portion coupled to the proximal portion of the first catheter section to couple the first and second drive means together. The coupled drive means are adapted to move the working means with respect to the material while the working means is advanced into the material to open the restriction.

BRIEF DESCRIPTION OF THE DRAWINGS

FIG. 1 is an illustration of a portion of the human vascular system and showing one possible site for introduction of a recanalization catheter device of the invention;

FIG. 2 is a sectional view of an artery and showing the cutting tip and distal end of the catheter located at the site of an atherosclerotic deposit;

FIG. 2A is a sectional view taken on the line 2A—2A of FIG. 2 to show the fluid passageway;

FIG. 3 is an end view of the cutting tip;

FIG. 4 is an end view of the device with the rotatable cutting tip removed;

FIG. 5 is an exploded perspective view of the distal end of the catheter and of the cutting tip;

FIG. 6 is a sectional view similar to FIG. 2 but showing another embodiment of the invention;

FIG. 6A and 6B are sectional views taken on the lines 6A—6A and 6B—6B of FIG. 6 to show the fluid passageways;

FIG. 7 is an exploded perspective view of the device of the second embodiment;

FIG. 8 is a sectional view similar to FIG. 2 but showing another embodiment of the recanalization catheter of the invention;

FIG. 9 is a longitudinal sectional view partially broken away, showing the embodiment of the device of FIG. 8 and including means for blocking the passageway distally of the catheter working head;

FIG. 10 is a longitudinal sectional view similar to that of FIG. 9 and showing the embodiment therein;

FIG. 11 is an enlarged sectional view taken along line 11—11 of FIG. 10;

FIG. 12 is a sectional view similar to that of FIG. 11 but showing an alternative embodiment of a portion of the device shown in FIGS. 9 and 10;

DETAILED DESCRIPTION OF THE PREFERRED EMBODIMENT

Figure 13:
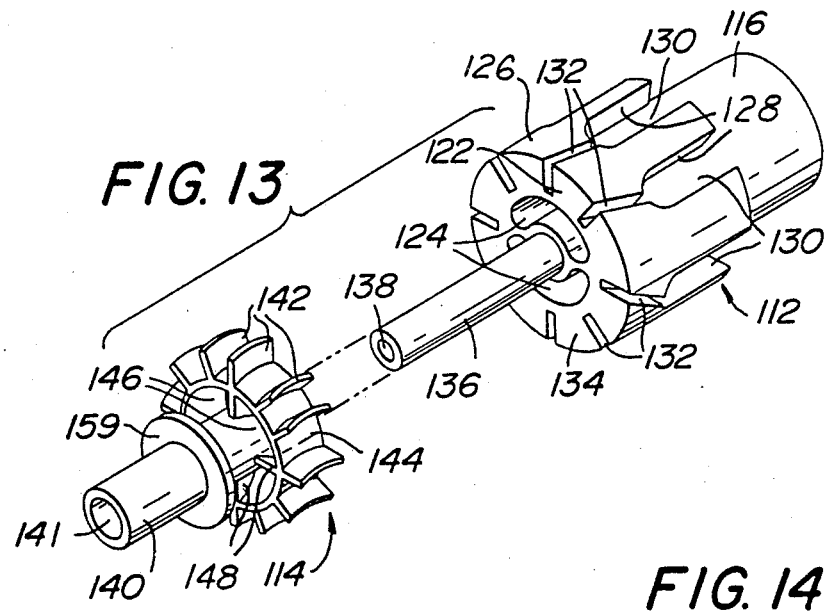
FIG. 13 is an exploded perspective view of a portion of the working head of the catheter shown in FIGS. 8-10.

In FIG. 1, there is shown a portion of the vascular system of the human body, illustrating one possible application for the method and device of the invention. Referring to FIG. 1, the device of the invention, which is indicated generally by the reference numeral 10, is a flexible recanalization catheter that is introduced into the femoral artery 12 at a point in the groin of the patient remote from the site of a blockage that has been determined to exist in a coronary artery, for example. The device 10 is then passed via the aorta 14 into the heart 16 and into the desired coronary artery to the site of the blockage.

In FIG. 2, there is illustrated a coronary artery 18 which contains a restriction, e.g., partial occlusion or blockage due to a deposit of atherosclerotic plaque 20. FIG. 2 shows the distal end of the device 10 at the site of the blockage caused by the plaque 20. The device 10 consists of a multiple-walled, flexible catheter that has an outer wall 22, and a first inner wall 24 that provides an outer passageway 26 extending throughout the length of the catheter. In addition, the device 10 has an inner tube 28 spaced from the inner wall 24 that provides a relatively large annular passageway 30. Tube 28 also defines a return passageway 32.

The outer passageway 26 terminates in a thin, flexible, annular member 34 the distal end of which is sealed. Thus, fluid pressure introduced into the outer passageway 26 at the proximal end of the device 10 will cause the flexible member 34 to expand or "balloon" throughout its entire circumference. The purpose of this balloon will be described hereinafter.

At the distal end of the device, there is affixed a rigid head 36 which has an inner tube, 38 the diameter of which corresponds to the diameter of tube 28. An annular passageway 40 is thus formed in head 36, which passageway 40 is in direct communication with the passageway 30 when the head is affixed to the distal end of the device as shown in FIG. 2. Inner tube 38 also provides a passageway 39 that communicates with return passageway 32 of the catheter. The head 36 is affixed to the distal end of the catheter in any suitable manner so as to provide a fluid tight seal.

Head 36 also has a front wall 42 from which extends a hollow shaft 44 that contains passageway 46 extending through the front wall 42 and connects with annular passageway 40 via angular passageway 48.

Front wall 42 of head 36 is relatively thick as shown in FIG. 2, and has formed in it a plurality of passageways 50. As best seen in FIG. 3, each passageway 50 terminates in the outside face of front wall 42 in an oval-shaped opening 52 and in the corresponding opening 54 in the inside face of wall 42, which openings 52 and 54 are offset circumferentially for purpose that will be evident from the description of the rotating cutting head hereinafter. Passageways 50 provide communication from the annular passageway 40 through the front wall 42. In addition, front wall 42 also contains on opposite sides of the shaft 44 somewhat kidney-shaped passageways 56 which provide communication through front wall 42 to the return passageway 39.

Mounted for rotation on shaft 44 is a rotating cutting head indicated generally by the reference numeral 58. Cutting head 58 has a main body portion 60 joined to the tubular portion 62 that engages the shaft 44. The rotating cutting head 58 is retained on the shaft 44 by use of a thrust washer 64 and wire 66 passing through holes in the outer end of shaft 44. A bonnet 68 is then by a press fit slipped over the end of the shaft 44 so as to present a smooth uninterrupted surface on the end of the device.

The rotating cutting held 58 has a pair of cutting blades 70 extending radially outwardly in opposite directions from the tubular portion 62. The cutting surface 72 of these blades converges from the front surface of the main body 60 to the outer end of the tubular portion 62 as best seen in FIG. 5.

The main body 60 of the rotating cutting head 58 also contains a plurality of outer passageways 74 in which are formed angular turbine blades 76. The outer passageways 74 correspond to the spacing of the openings 52 in the head 36, and because of the angularity of passageways 50 fluid flowing through passageways 50 will strike the angular turbine blades 76 so as to impart rotating motion to the cutting head 58.

The cutting head 58 also contains a plurality of angled holes 78 which are angled relative to wall 42. These angled holes 78 capture fluid in an axial pumping fashion and discharge the fluid into passageways 56 in head 36.

The general operation and use of the apparatus of the invention will now be described. After insertion of the apparatus at the appropriate selected site, such as into the femoral artery 12 (FIG. 1), the apparatus is then passed via the aorta 14 into the coronary artery 18 until it reaches the partial occlusion or blockage formed by the deposit of atherosclerotic plaque 20. Introduction of the apparatus can be aided by fluorosope, and the contrast medium can be introduced through the passageway 30.

Positive controlled pressure is then applied through the passageway 30 of the catheter which pressure will cause rotation of the cutting head 58 by application of the pressure to the angular turbine blades 76. Simultaneously, the angled holes 78 will induce return flow to the proximal end of the device, acting like an axial flow pump. This flow will pass through kidney ports 56. If necessary, negative pressure can be applied at the proximal end. The return flow will serve to aspirate the particles of plaque being cut away by the rotating cutting head 58, and the pressure differential created by application of positive pressure through the annular passageway 30 will also serve to pull the plaque 20 into a cutting position in the path of the cutting blades 70. During the cutting procedure, positive pressure introduced through the annular passageway 30 will not only serve to drive the rotating cutting head 58, but the fluid infused through this passageway can be oxygenated to eliminate distal ischemia during the procedure. Also, if desired, nitrates, contrast media or any other drugs can be added to the fluid as needed during the procedure. The entire procedure is preferably performed under fluoroscopic control so that the surgeon can determine when the blockage has been completely cut away. Of course, once the blockage has been completely removed to the satisfaction of the surgeon, the apparatus is withdrawn.

Although the apparatus and method of the invention provides minimal risk compared to angioplasty and bypass surgery, it is always possible that an artery wall weakened by disease or containing a congenital defect can break resulting in internal hemorrhage. If this occurs, the flexible member 34 can be inflated through passageway 26 to prevent blood loss until an appropriate surgical procedure can be conducted to correct the break in the arterial wall.

The design of the apparatus of the invention is such that the rigid head 36 and the rotating cutting head 58 are the only rigid portions of the apparatus and these do not interfere with easy passage of the instrument through a tortuous artery. The design of the distal end of the device, and the design of the rotating cutting head alleviates the need for a guiding catheter and may even permit blind application of the device through a tortuous plaque infested artery.

In FIGS. 6 and 7, there are illustrated another embodiment of the invention in which the innermost passageway of the catheter is used for the application of the positive pressure and the exterior annular passageway is used as the return passageway. In this other embodiment, parts corresponding to those of the first embodiment will be referred to by the same reference numeral of the first embodiment but followed by the letter "a". Thus, the catheter has an outer wall 22a and a first inner wall 24a that provides an annular passageway 26a extending throughout the length of the catheter. In addition, the device has an inner tube 28a spaced from the inner wall 24a to define a large annular passageway 30a that in this second embodiment is the return passageway. Tube 28a also defines a center passageway 32a. The outer passageway 26a terminates in a thin, flexible annular member 34a the distal end of which is sealed.

At the distal end of the catheter, there is affixed a rigid head 36a which has an inner tube 38a providing a passageway 40a that is in direct communication with the passageway 32a. Head 36a has a front wall 42a which contains a plurality of circular passageways 50a that exit the fact of front wall 42a at an angle to the surface. The passageways 50a communicate with the return passageway 40a. Front wall 42a of head 36a also contain a plurality of inner passageways 56a. These passageways 56a are in compound angular relationship to the axis of head 36a, having a radially outward direction and a vortex direction. Fluid passing from passageway 39a exits from 56a in a manner such as to impart a spinning action to the fluid and to head 58a. See FIGS. 6 and 7.

A rotating cutting head 58a is mounted on the shaft 44a of head 36a, and has a main body 60a and a tubular portion 62a. A pair of cutting blades 70a diverge rearwardly from the tubular portion 62a. The main body 60a is of a smaller diameter than the diametral position of the passageways 50a so that the pasageways 50a communicate directly to the exterior of the device. Because of the angularity of the passageways 56a, positive fluid pressure discharged from these passageways will impinge on the plurality of angled turbine blades 76a causing the cutting head 58a to rotate.

Similar to the first embodiment, the rotating cutting head 58a is held in place on shaft 44a by means of a retaining ring and thrust washer 64a, a retaining wire 66a and a bonnet 68a.

As previously indicated, the apparatus of the second embodiment is used in the same manner as described for the first embodiment. However in this second embodiment, positive fluid pressure is applied through the inner passageway 32a of the catheter which positive pressure serves to drive the rotating cutting head 58a, while return is made through the outer annular passageway 30a. Also, the apparatus of the second embodiment, especially the rotating cutting head 58a, should be simpler and less expensive to manufacture.

Obviously, the particular size and shape of the components of the apparatus as well as the size of the catheter itself will vary according to the application and use of the device. Preferably, the size of the catheter should be kept close to the size of the internal diameter of the artery or other wall in which it is to be inserted in order to assure co-axial movement of the rotating cutting head and limit the amount of the lateral movement of the cutting blades so as to avoid direct contact of them with the arterial wall. Co-axial movement of the apparatus is also aided by the positive pressure applied through the catheter which should aid in directing the rotating cutting head to the center of the artery.

The design of the device is quite unique in that positive fluid pressure can be used to power the device, and the driving fluid can be used to infuse necessary or desirable drugs during the procedure. Also, the driving fluid can be oxygenated to profuse the distal myocardium thus eliminating time pressure on the surgeon and reducing the likelihood of any technical error. Also, for example, streptokinase can be infused if thrombosis should form in the artery. Nitrates can also be infused for vasodiletation, and calcium blockers may be used to prevent arterial spasm. In contrast to the angioplasty procedure, there is no pressure applied to the arterial walls, thus eliminating many of the complications associated with angioplasty such as blowout, emboli, intimal tearing, etc.

The application of positive and negative pressure necessary during the procedure can be easily accomplished and controlled through known procedures since the triple lumen catheter concept is presently in use in other applications and can be easily adapted when the method and apparatus of the invention is used.

In FIG. 8 there is illustrated a coronary artery 18 which contains a partial occlusion or restriction 20 formed by the deposit of atherosclerotic plaque or some other material(s), such as waxy and/or calcified atheroma, thickened and/or ulcerated intima, etc. In that figure the distal end of an alternative embodiment of the recanalization catheter device constructed in accordance with the invention is shown. That device is denoted by the reference numeral 100 and is shown located at the site of a restriction caused by plaque 20 or some other material(s). Like the catheters described heretofore the device 100 basically comprises a flexible catheter that has an outer wall or lumen 102 and a first inner wall or lumen 104. Between lumens 102 and 104 there is defined a relatively large annular outer passage 106 extending throughout substantially the entire length of the catheter, that is from the distal end portion shown in FIG. 8 to the proximal end portion (not shown). The passage 106 serves to carry a fluid to a manifold assembly 110, to be described later located at the distal end of the catheter and on which is mounted a movable working head 109, e.g., a rotary (also to be described later). The fluid provided to the manifold serves to effect the rotation of a turbine bladed, working head-mounting portion of the manifold to be described later. The fluid returns from the manifold assembly through the passage 108 forming the interior of lumen 104 through a location adjacent the proximal end of the catheter.

As can be seen clearly in FIG. 8, the manifold assembly 110 is located within fluid constraining means (to be described in detail later) at the distal end of the catheter. The manifold assembly is shown clearly in FIGS. 8 and 13 and basically comprises a stationary body member 112 and a rotary turbine head 114. The turbine head 114 serves as the mount for the working head or cutter. The body member 112 is a generally cylindrical element which includes an elongated annular wall 116 extending longitudinally in the distal direction. The wall 116 is arranged for connection to the catheter's inner lumen 104 to receive fluid flowing therethrough. To that end the free end 118 of the inner lumen 104 is snuggly fit and secured within the interior of the annular wall 116 so that the interior space 120 of the annular wall 116 is in fluid communication with the passageway 108 in the lumen. The distal end of the stationary body member 112 includes a front wall portion 122 from which the annular 16 projects. A pair of diametrically opposed kidney-shaped fluid return ports 124 are provided in the front wall. Each of the ports extends at an acute angle to the longitudinal central axis 123 of the catheter and terminates in communication with the interior 120 of member 112. Thus, each return port is in fluid communication with the return passageway 108 in the catheter's inner lumen.

As shown clearly in FIG. 13 the annular wall 116 includes a thickened peripheral wall portion 126 contiguous with the distal end of member 112 and in which are located plural peripherally disposed, fluid-supply slots 128. Each supply slot includes an elongated enlarged entrance 130 which terminates in a narrow jet slot 132. Each jet slot is disposed at an acute angle to the longitudinal axis of the device and terminates at the front face 134 of the member 112. An elongated cylindrical post bearing 136 projects distally from the center of the front face of the member 112 so that kidney shaped fluid return ports 124 extend substantially about the post bearing. A central opening 138 extends completely through the bearing 136 and is in communication with the hollow interior 120 of the stationary member.

The turbine head 114 is a generally cylindrical member having an elongated cylindrical shaft portion 140 which serves as the mount for the working head 109. The shaft 140 includes a central bore 141 extending completely therethrough and through which the post bearing of the stationary member 112 extends. The proximal end of the turbine head 114 includes a plurality of turbine blades 142 extending outward radially from a hub-like central section 144. Each blade is slightly curved in the longitudinal direction. The central hub portion 144 of the turbine head includes a plurality of angled curved passageways 146 formed between plural, equadistantly spaced, outwardly projecting sharply angled arcuate walls 148 (See FIG. 13). These passages serve as fluid return inducers. When the turbine head 114 is mounted on the post hearing of the stationary member 122 the inducer passages 146 of the turbine head are disposed opposite to the stationary kidney shaped return ports 124 while the turbine blades are disposed opposite to the jet slots 132.

The manifold assembly 110 is secured in place on the distal end of the catheter via the use of the heretofore identified fluid constraining means 111. That means basically comprises a shroud 150. The shroud's main purpose is to constrain the substantial portion of the turbine driving fluid within the catheter (for reasons to be described later). Basically the shroud is in the form of a tubular sleeve having a cylindrical sidewall 152, the proximal end 154 of which is internally threaded for securement to corresponding threads 156 on the distal end of the catheter's outer lumen 102. The stationary member 112 of the manifold assembly is located within the shroud 150 so that the peripheral surface of the wall portions 126 (FIG. 13) of that member located between adjacent supply slots is in a tight, press-fitting engagement with the interior surface of the shroud to secure the member therein. As can be seen in FIG. 8 the front end of the shroud is in the form of a planar endwall 157 having a central opening 158 through which the free end of the working head-mounting shaft 140 extends. A disk-like thrust annulus 159 extends radially outward from the tool mounting shaft 140 at an intermediate point therealong and engages the interior of the shroud's front wall contiguous with its central opening 158. The front wall of the shroud also includes a plurality of small outlet ports 160 whose function will also be described later.

Disposed on the free end of the shaft 140 is the working head 109, in this case rotary cutter 162. The cutter 162 constitutes one embodiment of my joint invention with another inventor in a rotary cutter for use in intravascular surgery and which is the subject of a patent application to be filed later. The specific cutter shown herein constitutes a dual-bladed embodiment of that joint invention.

Figure 15:
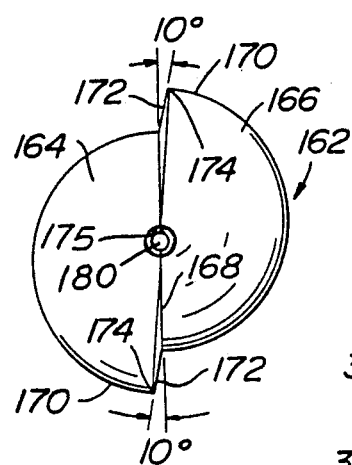
FIG. 15 is an enlarged front view of the distal end of the embodiment shown in FIG. 8.

As can be seen in FIGS. 8 and 15 the cutter 162 basically comprises a solid bodied element whose outer distal periphery is in the form of a pair of convex sections 164 and 166 which are slightly laterally offset from each other along a divider line 168. The intersection of the convex surface 170 of each section with a planar surface 172 contiguous with a divider line 168 forms an arcuate cutting edge or blade 172. in accordance with the teachings of my aforementioned joint invention the cutter may be made up of any number of sections, thereby forming a device having any number of arcuate blades, with each blade preferably including at least one portion having a negative or zero degree rake. In the embodiment shown herein each blade is at a negative rake angle of 10°.

The cutter 162 also includes a central hole 175 extending therethrough. The hole 175 includes an enlarged bore 176 which extends into the body of the cutter from the proximal face thereof. The shaft 140 of the turbine member 112 is disposed within the bore 176 to mount the cutter thereon.

The catheter 100 is arranged to be guided to its operative position within the artery 18 by the use of an elongated guidewire 180. This action is accomplished by inserting the guidewire 180 at the appropriate selected site in the body, such as into the femoral artery 12 (FIG. 1). The guidewire is then passed via the aorta 14 into the coronary artery to the location of the partial occulsion or blockage 20. Introduction of the guidewire can be aided by a fluoroscope, and a contrast medium can also be introduced into the artery. The catheter 100 is then threaded down the guidewire 180, via the opening 175 in the cutter, the opening 141 in the manifold assembly, and the hollow interior of inner lumen 104, to a position wherein the cutter 162 is located immediately adjacent the proximal end of the restriction 20. Fluid then is introduced into the passage 106 by means (not shown) from a point adjacent the proximal end thereof. The fluid flows down the passage 106 in the direction of the arrows and is controlled by means (not shown) so that controlled positive pressure is applied to the manifold assembly. In particular the fluid flows into the supply slots 128 between the outer surface of tube portion 116 and the inner surface of the shroud's sidewall. The fluid then accelerates through the communicating jet slots and exits those slots as plural jet streams, each extending at an acute angle to the longitudinal axis 123 of the catheter. These angularly directed jet streams impinge the turbine blades 142 disposed immediately adjacent thereto to impart rotary motion to the turbine head 114 and hence to the cutter 162 mounted thereon.

Absent the fluid constraining function provided by the shroud 150 the amount of fluid flow required to provide sufficient power for effectively driving the working head may be too much for some distally located tissues to absorb. Thus, the shroud 150 serves to constrain or contain most of the driving fluid within the catheter. However, a small portion of the driving fluid does exit the distal end of the catheter through the shroud's openings 160. The fluid exiting these openings flows into the interface between the cutter 162 and the front wall of the shroud. This action has the advantageous effect of providing positive pressure to the wall of the artery, thereby causing the artery wall to move slightly outward radially, that is away from the device so that damage to the artery walls by the cutter does not occur. In addition the flow of fluid outward through the interface of the catheter and shroud also precludes fine fiberous tissuse of the artery from gaining ingress into the interface where it could snag or spool up. Moreover, the rotating cutter blades impart momentum to the exiting fluid, which action applies further positive pressure to the artery walls, thereby further decreasing the chances of tissue-snagging.

With the bulk of the fluid constrained within the catheter the angled orientation of the return inducer passages 146 act like an axial flow pump to induce a reverse flow of the fluid back toward the proximal end of the catheter. In particular the fluid flows from the inducer passages 146 into the immediately adjacent kidney shaped return ports 124 and from there into the chamber 120 and finally into the return flow passage 108 in the inner lumen 104.

As can be seen by the arrows in FIG. 8 some fluid also flows out of the distal end of the device via the aligned central openings 141 and 175. This fluid can be used to profuse downstream (distal) tissue. Thus, like the embodiment shown and described with reference to FIGS. 1-7, the fluid used to power the catheter 100 may be oxygenated, may include drugs or medicines, or contrast media, or combinations thereof for introduction into the artery via the openings 160 and 175.

The restriction opening process is carried out by advancing the catheter as its cutter rotates into the material making up the restriction so that the rotating cutter blades engage that material. In some instances, e.g., hard or calcified deposits, the opening is created by the rotating cutter actually cutting away or emulsifying particles of the material(s) making up the restriction. In other instances, e.g., waxy or soft deposits, the material(s) of the restriction may merely be mechanically agitated, beaten or otherwise disturbed by the blades of the rotating cutter, whereupon an opening is created by the movement of the material(s) without it actually being cut up or removed from the restriction. In either case an opening permitting the freer flow of blood through the restriction results.

As can be seen in FIG. 8 the radial distance to the cutting edge 174 of each blade immediately adjacent to the proximal end of the cutter when measured from the longitudinal central axis 123 is slightly longer than the radial distance from that axis to the outside surface of the sidewall 154 of the shroud. This feature insures that a slight space is created between the inner surface of the artery wall and the entrance to the interface between the cutter and the end of the shroud, again in the interest detering any snagging or spooling action of the fiberous tissue of the artery wall within the interface.

As a further aid in profusing distally located tissue with either oxygenated fluid, drugs, contrast media or dyes the guidewire 180 may be replaced by a flexible hollow guide tube (not shown) for directly carrying such fluids distally of the cutting head.

In FIG. 9 there is shown yet another embodiment of the recanalization catheter in this invention. In the embodiment shown therein the catheter 100 described heretofore is used in combination with means 200 for blocking the artery 18 distally of the restriction to preclude any particles, e.g., emboli, of the restriction removed during the restriction opening process from flowing distally. Thus, the embodiment of FIG. 9 is of particular utility for surgical applications involving the removal of heavy atherosclerotic deposits in an artery that is sensitive to the escape of emboli downstream of the restriction. One such application is the opening of restrictions in carotid arteries.

As can be seen in FIG. 9 the blocking means 200 basically comprises a multi-lumen tube 202 and a balloon 204. The tube 202 extends through the length of the catheter 100, that is through the catheter's inner lumen 104, the manifold assembly opening 141 and the cutter opening 175 and terminates in an end portion lying distally beyond the restriction 20. The balloon is mounted on that end portion of the tube and serves as an expandable passageway blocking member. To that end the balloon is a hollow, inflatable member having a pair of openings 206 through which a distal portion of the multi-lumen tube 202 extends. The wall portion of the balloon contiguous with the periphery of each opening 206 is sealed at 208 to the periphery of the outer surface of the tube 202. The balloon is formed of a material and is configured in size so that when it is inflated by a fluid, in a manner to be described later, it completely expands to fill the artery 18, that is the periphery 210 of the balloon engages the inner surface, e.g., intima, of the artery about the entire periphery of the artery and without stretching of the material forming the balloon. Inflatation of the balloon is effected by means of inflation/-deflation ports 212 provided in an inflation passageway 214 in the multi-lumen tube. The ports 212 are in communication with the interior of the balloon and with the passageway 214. The passageway 214 extends longitudinally down the length of the multi-lumen tube 202 from a point (not shown) adjacent the proximal end of the catheter to a point 216 just distally of the balloon, at which point the passageway 214 is sealed. Fluid is provided down the passageway 214 from a proximal location to effect the inflation of the balloon. Conversely the balloon is deflated by drawing the fluid from the balloon's interior out through passageway 214.

The multi-lumen tube 202 also includes a second passageway extending throughout the length of tube 202. A tube 218 also of the length of tube 202 is disposed within this second passageway and terminates at an open end 220 located distally of the balloon 204. The tube 218 serves as a passageway for the flow of a profusion fluid into the artery distally of the restriction as well as a guide (similar to guidewire 180 described heretofore) to facilitate the placement of the catheter's working head just proximally of the restriction and with the balloon placed just distally thereof.

Operation of the recanalization catheter 100 and blocking means 200 described heretofore is as follows: The guide/profusion tube 218 is threaded through the artery to the site of the restriction, e.g., stenosis. The multi-lumen tube 202 with the balloon 204 at the distal end thereof is then threaded over the guide tube 218 until the balloon is just distally of the stenosis. Blood or oxygen saturated fluid is then passed through the tube 218 to flow out the open end 220 thereof so as to pass distally into the artery. The balloon 204 is inflated, via the passage of fluid through the inflation passageway 214, until the periphery of the balloon engages the interior periphery of the artery distally of the restriction. The recanalizing catheter 100 is then passed over the multi-lumen tube 202 until its cutter 162 is located immediately adjacent the restriction on the proximal side thereof. The turbine of the catheter is then driven by the introduction of fluid into the passageway 106 while the catheter is advanced into the restriction to effect the opening thereof. Any particles or emboli of the stenosis cut away or emulsified by the blades of the cutter are precluded from flowing distally of the restriction by the expanded balloon. Once the restriction has been opened the recanalizing catheter 100 is removed, with the blocking means left in place and its balloon 204 still expanded. Debris created by the restriction opening process can then be aspirated by the introduction of a dual-lumen flushing/aspirating catheter (not shown) into the artery. This is accomplished by passing the flushing/aspirating catheter over the multi-lumen tube 202. The flushing/aspirating catheter can be of any construction so long as it includes one passageway for carrying a flushant under pressure to the site of the opened stenosis and a second passageway which can be placed under suction to aspirate that site. Once flushing and aspiration is completed the balloon 204 is deflated and the blocking means 200 is removed.

It must be pointed out at this juncture that the multi-lumen tube 202 be made to include another longitudinally extending passageway to serve as a flushant return line (aspiration line) thereby obviating the need for a dual lumen flushing/aspirating catheter. In FIGS. 10 and 11 there is shown blocking means 200 incorporating such a feature. In that embodiment the balloon 204 is mounted on an alternative multi-lumen tube 222. The multi-lumen tube 222 is clearly shown in FIG. 11, and includes a longitudinally extending passage 224 throughout its length and through which the guide/-profusion tube 218 extends. The multi-lumen tube 222 also includes the heretofore identified longitudinally extending inflation/deflation passageway 214. Finally the tube 222 includes a longitudinally extending aspiration or suction return passageway 226. The passageway 226 is closed at its end 228 but inludes an access or entrance port 230 located just proximally of the location of the balloon 204. The port 230 serves as the opening into which any emboli-bearing fluid passes for subsequent flow down the tube 226 to a proximal location for removal.

In FIG. 12 there is a sectional view similar to FIG. 11 but showing yet another alternative multi-lumen tube for the blocking means 200. This alternative embodiment not only contains the heretofore identified profusion/guide tube 218, the inflation/deflation passageway 214, and the aspiration passageway 226, but also contains a flushant carrying pasageway 232. The flushant passageway 232 is similar in construction to passageway 226 and thus includes an outlet port 234 open to the site of the restriction. The outlet port is located adjacent the inlet port 230. With the embodiment of FIG. 12 a flushant fluid can be provided down the length of the pasage 232 and out through port 234 to flush away any emboli or particules created at the site of the restriction.

It should be appreciated by those skilled in the art that the fluid utilized to drive the catheter's turbine can also be used as the flushant inasmuch as a portion of the driving fluid does, in fact, gain egress from the interior of the catheter at the location of the cutting head, as described heretofore.

As should also be appreciated by those skilled in the art the recanalization catheters described heretofore have inherent limitations insofar as the physical size and radius of passageways, e.g., arteries, which can be negotiated to locate the working head at the site of a restriction to be opened. Thus, in operating on restrictions located in very small arteries located a substantial distance from the point at which the recanalization catheter is to be introduced into an artery a turbine driven recanalization catheter may not be practical. In this regard, as is known hydraulic turbines do not scale down well, that is they lose efficiency with decreasing size. Moreover due to the need to have two flow paths, that is one to the turbine and the other from the turbine, such catheters cannot be made too long since viscous fluid losses become severe in long catheters. On the other hand elongated flexible wire drives can be made of small diameter but long length without a substantial loss of efficiency. In this regard the co-inventor of the cutter described heretofore has made an invention in a rotary wire-driven intravascular recanalization catheter and which is also the subject of a patent application to be filed later. That catheter includes a rotary working head, like that described heretofore, and which is driven by an elongated rotating wire which extends from the working head the length of the catheter to a source of power located at the proximal end of the catheter. Bearing means are provided in the catheter to insure that the wire is kept centered and spins freely without going into critical whirl. Catheters constructed in accordance with that invention can be made very small in diameter and long in length in the interest of flexibility yet can produce sufficient power at the working end to efficiently open a restriction in even very small remotely located passageways. While such rotary tool wire-drives can be made quite small in diameter, it is difficult to make such drives of large diameter for very high power transmission without a sacrifice in flexibility and ease of placement in an artery, inasmuch as an increase in wire thickness necessarily results in a decrease in the radius of bend for the same amount of strain.

Figure 14:
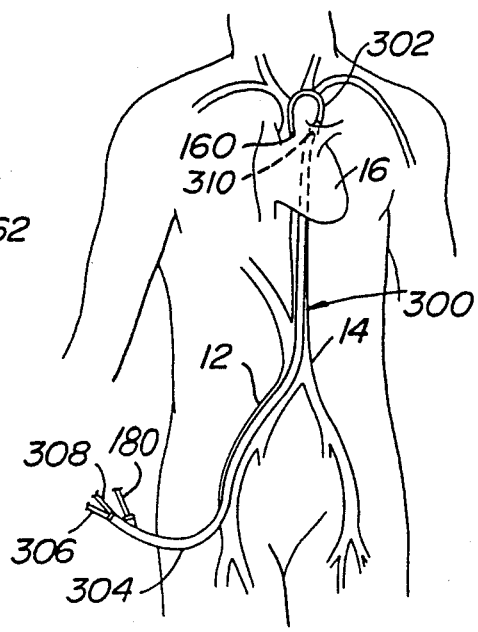
FIG. 14 is illustration of a portion of the human vascular system and showing the use of yet another alternative embodiment of the invention.

In view of the above factors and in accordance with another aspect of this invention, in FIG. 13 there is shown a combination recanalization catheter 300 arranged to provide high power to a small diameter working head over a substantial distance from a source of power. Thus the catheter 300 is arranged to be introduced into the body at the site of a large diameter passageway, e.g., a femoral artery, and for extending through the body to the site of a restriction in a small, remotely located artery, e.g., coronary artery. That catheter includes two, serially-connected, elongated sections, namely, a distal section 302 and a proximal section 304. The distal section 302 is a short, flexible member including a rotary working head, e.g., like the cutter 162 described heretofore, located at the distal end and which is driven by a rotating wire (not shown) extending down the length of the section within the interior thereof. The wire driven section 302 is of small diameter in the interest of negotiating small passageways, such as coronary arteries. The proximal end of the distal section 302 is connected to the distal end of proximal section 304 via a turbine coupling 310. The turbine coupling includes a turbine head (not shown) to which the wire drive is coupled. The proximal section 304 is arranged to transmit high power over a substantial distance to the distal section of the catheter. Thus the proximal section is a larger diameter, long catheter section which includes a first passage 306 extending therethrough for carrying a turbine driving fluid under pressure down the section to the turbine coupling to cause its rotation, and a second passageway 308 extending through the section for returning the turbine driving fluid back to the proximal end of the section. The combination recanalization catheter 300 shown in FIG. 14 also includes a passageway (not shown) through which a guide wire 180 extends to guide the catheter into position like that described heretofore.

While the catheter 300 has been described being made up of a wire drive section 302 and a turbine drive section 304, it should be clear that either section can be wire drive or turbine drive, depending upon the application.

Although the invention is described in connection with certain preferred embodiments and for the particular purpose of removing atherosclerotic plaque, it will, however, be evident to those skilled in the art that the method and apparatus of the invention has application for treatment of conditions other than atherosclerosis. Moreover, the described method and technique for the removal of atherosclerotic tissue is not limited to any particular texture of tissue and is applicable to all atherosclerotic processes. It is further contemplated that the method and apparatus of the invention will have applications outside of human medicine as well as many applications for treatment of many conditions in the human body. Obviously, the specific size and design of the catheter and working head, e.g., cutting tip, and the specific design of the rotating cutting blades will depend upon the particular application of the invention.

Having thus described the invention, it will be obvious to those skilled in the art that various revisions and modifications can be made to the preferred embodiments described herein without departing from the spirit and scope of the invention. It is my intention, however, that all such revisions and modifications as are obvious to those skilled in the art will be included within the scope of the following claims.

I claim:

1. A method of opening a restriction formed of material inside of a vessel within a living being, said vessel being formed of a tubular wall of tissue and having a longitudinal axis extending down its length, the inside diameter of said vessel being substantially smaller than its length, said method comprising: guiding a catheter having a longitudinal axis and rotatable working means located at a distal end portion thereof through said vessel along said longitudinal axis to the location of said restriction; applying a first fluid in said catheter and rotating said working means about said axis; advancing said catheter with said working means rotating about said axis and with respect to said material into said material while directing at least a portion of said fluid outward with respect to said axis to apply positive pressure to said vessel wall adjacent said working means to cause said vessel to move slightly outward radially with respect to said axis thereof, whereupon said restriction is opened, said positive pressure also acting to prevent damage to the tissue making up said vessel during said restriction opening.

2. The method of claim 1 wherein said vessel is a blood vessel.

3. The method of claim 1 additionally comprising the step of precluding any material loosened during said restriction opening from flowing distally beyond the location of said restriction.

4. An apparatus for opening a restriction formed of material inside a vessel within a living being, said vessel being formed of a tubular wall of tissue and having a longitudinal axis extending down its length, the inside diameter of said vessel being substantially smaller than its length, said apparatus comprising: an elongated catheter having a longitudinal axis and a distal portion including movable working means located thereat, said catheter being flexible to conform to the tortuosity of said vessel to enable said catheter to be readily slid down said vessel along the axis thereof to the position wherein said movable working means is located adjacent said restriction, said movable working means including an end portion arranged to be rotated about the longitudinal axis thereof by means located within said catheter, means for supplying a fluid through said catheter to said end portion as said end portion is rotated about said axis and advanced into said material, said last mentioned means being arranged to cause said fluid to flow outward with respect to said axis all the while said end portion is rotating to supply positive pressure to said vessel adjacent said end portion to cause said vessel to move slightly outward radially with respect to the axis thereof, whereupon said restriction is opened, said positive pressure also acting to prevent damage to the tissue making up said vessel as said restriction is opened.

5. The apparatus of claim 4 additionally comprising blocking means located distally of the location of said restriction.

6. The apparatus of claim 5 wherein said blocking means is disposed on a distal end portion of another catheter located within said vessel.

7. The apparatus of claim 6 wherein said blocking means is actuatable.

8. The apparatus of claim 6 wherein said catheter includes a passage extending longitudinally therethrough and through which said other catheter passes.

9. The apparatus of claim 4 wherein said catheter includes first and second catheter sections, said first catheter section having drive means, a proximal end portion, and a distal end portion at which said working means is located, said second catheter section having drive means, a proximal end portion, and a distal end portion, said distal end portion of said second catheter section being coupled to the proximal portion of said first catheter section to couple the drive means of said first catheter section to the drive means of said second catheter section whereupon said coupled drive means effect the rotation of said working means, said first catheter section being of smaller outside diameter than said second catheter section.

10. The apparatus of claim 9 wherein at least one portion of said coupled drive means comprises fluid pressure drive means.

11. The apparatus of claim 10 wherein said second drive means comprises fluid pressure drive means.

12. An apparatus for opening a restriction formed of material inside a vessel within a living being, said vessel being formed of a tubular wall of tissue and having a longitudinal axis extending down its length, the inside diameter of said vessel being substantially smaller than its length, said apparatus comprising: an elongated catheter having a longitudinal axis and a distal portion including movable working means located thereat, said catheter being flexible to conform to the tortuosity of said vessel to enable said catheter to be readily slid down said vessel along the axis thereof to the position wherein said movable working means is located adjacent said restriction, said movable working means including an end portion arranged to be rotated about the longitudinal axis thereof by means located within said catheter, means for supplying a fluid through said catheter to said end portion as said end portion is rotated about said axis and advanced into said material, said last mentioned means being arranged to cause said fluid to flow outward with respect to said axis all the while said end portion is rotating to supply positive pressure to said vessel adjacent said end portion to cause said vessel to move slightly outward radially with respect to the axis thereof, whereupon said restriction is opened, said positive pressure also acting to prevent damage to the tissue making up said vesesl as said restriction is opened, and said catheter further comprises a proximal portion and a first passage extending through said catheter from the proximal portion to the distal portion, said passage carrying a first fluid to said working means to cause the rotation thereof.

13. The apparatus of claim 12 wherein said catheter also comprises a second passage for carrying said first fluid away from said working means back to the proximal portion of said catheter.

* * * * *